(12) United States Patent
Kimura

(10) Patent No.: US 6,521,568 B1
(45) Date of Patent: Feb. 18, 2003

(54) PLANT DISEASE CONTROLLING COMPOSITIONS AND PLANT DISEASE CONTROLLING METHOD

(75) Inventor: Norio Kimura, Mino (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/111,009

(22) PCT Filed: Oct. 13, 2000

(86) PCT No.: PCT/JP00/07150

§ 371 (c)(1),
(2), (4) Date: Apr. 19, 2002

(87) PCT Pub. No.: WO01/28330

PCT Pub. Date: Apr. 26, 2001

(30) Foreign Application Priority Data

Oct. 21, 1999 (JP) ............................................. 11-299474

(51) Int. Cl.$^7$ ........................ A01N 43/56; A01N 43/38; A01N 43/76; A01N 47/38; C07D 23/52; C07D 405/04

(52) U.S. Cl. ..................... 504/130; 514/404; 548/368.7

(58) Field of Search ........................ 548/368.7; 514/404

(56) References Cited

U.S. PATENT DOCUMENTS 5,869,687 A * 2/1999 Sato et al. ................ 548/368.7
6,294,567 B1    9/2001 Hashizume et al. ........ 514/404

FOREIGN PATENT DOCUMENTS

| EP | 0679 643 A2 | 11/1995 |
|---|---|---|
| EP | 0741 970 A1 | 11/1996 |
| JP | 58-121202 A | 7/1983 |
| JP | 59-67206 A | 4/1984 |
| JP | 61-63607 A | 4/1986 |
| WO | 99/54307 A1 | 10/1999 |

* cited by examiner

*Primary Examiner*—Sabiha Qazi
(74) *Attorney, Agent, or Firm*—Birch, Stewart, Kolasch & Birch, LLP

(57) ABSTRACT

The present invention relates to a plant diseases controlling composition containing as active ingredients: the pyrazolinone derivative represented by Chemical Formula:

wherein
$R_1$ represents halogen or methyl optionally substituted with halogen, $R_2$ represents hydrogen, halogen or methyl optionally substituted with halogen, $R_3$ represents isopropyl, sec-butyl, 1-ethylpropyl, 1-methylbutyl, tert-butyl or 1,1-dimethylpropyl, $R_4$ representing oxygen or sulfur, $R_5$ represents C1–C5 alkyl, C2–C5 alkynyl or C3–C5 alkenyl, and at least one imide compound selected from N-(3,5-dichlorophenyl)-1,2-dimethylcyclopropane-1,2-dicarboximide, 3-(3,5-dichlorophenyl)-N-(1-methylethyl)-2,4-dioxo-1-imidazolidinecarboxamide and 3-(3,5-dichlorophenyl)-5-methyl-5-vinyl-1,3-oxazolidine-2,4-dione;

and a plant diseases controlling method comprising applying said pyrazolinone derivative with said imide compound. The present invention can effectively control plant diseases.

10 Claims, No Drawings

PLANT DISEASE CONTROLLING COMPOSITIONS AND PLANT DISEASE CONTROLLING METHOD

This application is the national phase under 35 U.S.C. §371 of PCT International Application No. PCT/JP00/07150 which has an International filing date of Oct. 13, 2000, which designated the United States of America.

TECHNICAL FIELD

The present invention relates to a plant diseases controlling composition and a plant diseases controlling method.

BACKGROUND ART

Various plant diseases controlling agents have been developed for controlling plant diseases, but a plant diseases controlling agent having higher activity is always requested.

DISCLOSURE OF THE INVENTION

The aim of a present invention is to provide a plant diseases controlling composition having high activity and a method for controlling efficiently plant diseases.

The present inventor has studied to control plant diseases, as a result, he has found that high synergistic effect for controlling plant diseases could be achieved by using some species of pyrazolinone derivatives and specific imide compounds together.

That is to say, the present invention provides a plant diseases controlling composition (hereinafter, referred to as the composition of the invention) comprising:

at least one imide compound selected from N-(3,5-dichlorophenyl)-1,2-dimethylcyclopropane-1,2-dicarboximide (hereinafter, referred to as the Compound II)), 3-(3,5-dichlorophenyl)-N-(1-methylethyl)-2,4-dioxo-1-imidazolidinecarboxamide (hereinafter, referred to as the Compound (III)) and 3-(3,5-dichlorophenyl)-5-methyl-5-vinyl-1,3-oxazolidine-2,4-dione (hereinafter, referred to as the Compound (IV)); and the pyrazolinone derivative (hereinafter, referred to as the Compound (I)) represented by Chemical Formula:

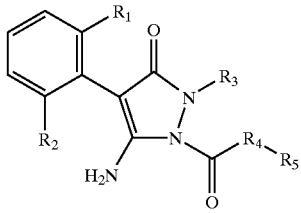

(I)

wherein
R$_1$ represents halogen or methyl optionally substituted with halogen, R$_2$ represents hydrogen, halogen or methyl optionally substituted with halogen, R$_3$ represents isopropyl, sec-butyl, 1-ethylpropyl, 1-methylbutyl, tert-butyl or 1,1-dimethylpropyl, R$_4$ represents oxygen or sulfur and R$_5$ represents C1–C5 alkyl, C2–C5 alkynyl or C3–C5 alkenyl;
as active ingredients.

And also it provides a method (hereinafter, referred to as the method of the invention) for controlling plant diseases by applying at least one imide compound selected from the Compound (II), the Compound (III) and the Compound (IV); and the Compound (I); to plant(s), to land where plant(s) is growing or to seeds of plant.

THE BEST MODE FOR CARRYING OUT THE INVENTION

At first the Compound (I) is described.

In the definition of R$_1$ and R$_2$ in the Chemical Formula (I); halogen includes fluorine, chlorine and the like, methyl optionally substituted with halogen includes methyl, trifluoromethyl, trichloromethyl and the like. In the definition of R$_5$; C1–C5 alkyl includes methyl, ethyl, propyl, butyl and the like, C2–C5 alkynyl includes 2-propynyl, 2-butynyl, 3-butynyl and the like, C3–C5 alkenyl includes 2-propenyl, 2-butenyl, 3-butenyl and the like.

Preferred compounds among the Compound (I) is the compound wherein R$_1$ is chlorine, R$_2$ is chlorine, R$_3$ is sec-butyl, R$_4$ is sulfur and R$_5$ is ethyl.

The compound represented by Chemical Formula (I) can exist as tautmers represented below. In this description, "the Compound (I)" extends all of these tautmers.

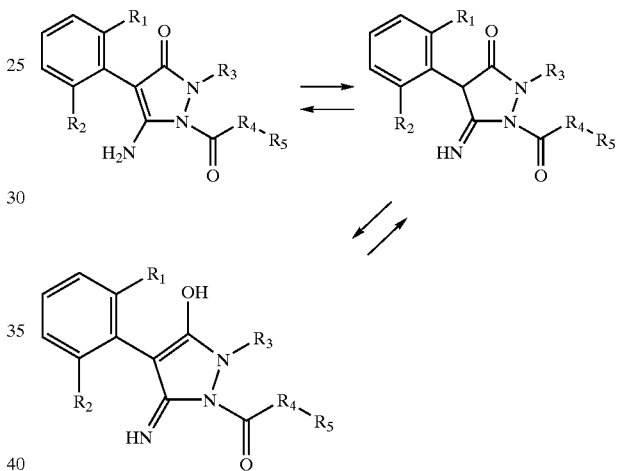

While sometimes streoisomers originated from (a) double bond(s) or from (an) asymmetric carbon(s) may exist in the compound represented by Chemical Formula (I), "the Compound (I)" extends to all of these streoisomers and the mixtures of at least two these stereismers.

Examples of the Compound (I) are listed in Table 1 together with compound numbers.

TABLE 1

| Compound number | R$_1$ | R$_2$ | R$_3$ | R$_4$ | R$_5$ |
|---|---|---|---|---|---|
| (I-a) | Me | H | iso Pr | O | Et |
| (I-b) | Me | H | sec Bu | O | Et |
| (I-b(+)) | Me | H | sec Bu | O | Et |
| (I-b(−)) | Me | H | sec Bu | O | Et |
| (I-c) | Cl | H | iso Pr | O | Et |

TABLE 1-continued

[Structure: pyrazole with R1, R2 on phenyl; R3 on N; R4, R5 and C=O; H2N group]

| Compound number | R₁ | R₂ | R₃ | R₄ | R₅ |
|---|---|---|---|---|---|
| (I-d) | Cl | H | sec Bu | O | Et |
| (I-d(+)) | Cl | H | sec Bu | O | Et |
| (I-d(−)) | Cl | H | sec Bu | O | Et |
| (I-e) | Cl | Cl | iso Pr | O | Et |
| (I-f) | Cl | Cl | sec Bu | O | Et |
| (I-f(+)) | Cl | Cl | sec Bu | O | Et |
| (I-f(−)) | Cl | Cl | sec Bu | O | Et |
| (I-g) | Cl | Cl | iso Pr | O | CH₂—CH=CH₂ |
| (I-h) | Cl | Cl | sec Bu | O | CH₂—CH=CH₂ |
| (I-h(+)) | Cl | Cl | sec Bu | O | CH₂—CH=CH₂ |
| (I-h(−)) | Cl | Cl | sec Bu | O | CH₂—CH=CH₂ |
| (I-i) | Me | H | iso Pr | S | Et |
| (I-j) | Me | H | sec Bu | S | Et |
| (I-j(+)) | Me | H | sec Bu | S | Et |
| (I-j(−)) | Me | H | sec Bu | S | Et |
| (I-k) | Cl | H | iso Pr | S | Et |
| (I-l) | Cl | H | sec Bu | S | Et |
| (I-l(+)) | Cl | H | sec Bu | S | Et |
| (I-l(−)) | Cl | H | sec Bu | S | Et |
| (I-m) | Cl | Cl | iso Pr | S | Et |
| (I-n) | Cl | Cl | sec Bu | S | Et |
| (I-n(+)) | Cl | Cl | sec Bu | S | Et |
| (I-n(−)) | Cl | Cl | sec Bu | S | Et |
| (I-o) | Cl | Cl | iso Pr | S | CH₂—CH=CH₂ |
| (I-p) | Cl | Cl | sec Bu | S | CH₂—CH=CH₂ |
| (I-p(+)) | Cl | Cl | sec Bu | S | CH₂—CH=CH₂ |
| (I-p(−)) | Cl | Cl | sec Bu | S | CH₂—CH=CH₂ |

In Table 1, "Me" represents methyl, "Et" represents ethyl, "sec Bu" represents sec-butyl and "iso Pr" represents isopropyl. And a symbol of (+) in the compound number indicates that the compound is a optically active substance which shows plus optical rotation (solvent: methanol). A symbol of (−) in the compound number indicates that the compound is a optically active substance which shows minus optical rotation (solvent: methanol).

Next, a Production Example for the Compound (I) are described below.

Production Example 1

Step (1)

Zero point nine eight (0.98) g (3.29 mmol) of bis(trichloromethyl)carbonate was dissolved in 10 ml of 1,4-dioxane, to which 0.79 g (10.0 mmol) of pyridine was added dropwise under cooling with water. After stirring at room temperature for 30 minutes, 1.35 g (10.0 mmol) of 2-propene-1-thiol was added dropwise, and additional 30-minutes stirring at room temperature, the reaction solution was filtered to obtain a filtrate (hereinafter, referred to as "filtrate A").

Step (2)

Three hundred (300) ml of 3N hydrochloric acid and 100 ml of ethanol were added to 107 g (313 mmol) of 3-amino-2-tert-butyl-1-isopropyl-4-(2,6-dichlorophenyl)-3-pyrazoline-5-one and stirred under the refluxing condition for 4 hours. Then ethanol was distilled off under reduced pressure and the aqueous layer was neutralized with a dilute sodium hydroxide solution. The precipitated solid was filtered out, washed with water and ethyl acetate, and dried in vacuo to obtain 88.4 g (309 mmol) of a compound described below.

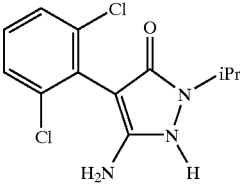

3-Amino-2-tert-butyl-1-isopropyl-4-(2,6-dichlorophenyl)-3-pyrazorine-5-one can be prepared according to the method(s) described in JP-A-8-208621.

Step (3)

Twenty (20) ml of toluene was added to a mixture of 1.41 g (4.93 mmol) of the compound obtained at step (2) and 0.42 g (10.0 mmol) of lithium hydroxide monohydrate, and the mixture was refluxed for 30 minutes while removing water by azeotoropic dehydration. Then toluene was distilled off under reduced pressure and 10 ml of 1,4-dioxane was added to a residue. The "filtrate A" obtained at step (1) was added dropwise under the refluxing condition, and after additional 10-minute stirring under the refluxing condition, 1,4-dioxane was distilled off under reduced pressure. Water was added to a residue, the solution was extracted with ethyl acetate, and the organic layer was washed twice with water. Then the solvent was distilled off under reduced pressure and a residue was subjected to silica gel column chromatography to obtain 0.14 g (0.36 mmol) of the Compound (I-o).

m.p.: 170.80° C.

The Compound (I) except the Compound (I-o) can be prepared according to the method described above.

It is known that N-(3,5-dichlorophenyl)-1,2-dimethylcyclopropane-1,2-dicarboximide was as its common name of "procymidone", 3-(3,5-dichlorophenyl)-N-(1-methylethyl)-2,4-dioxo-1-imidazolidinecarboxamide as its common name of "iprodione" and 3-(3,5-dichlorophenyl)-5-methyl-5-vinyl-1,3-oxazolidine-2,4-dione as its common name of "vinclozolin". And these compound are commercially available compounds, described in the catalog of Farm Chemicals Handbook, 1999, C-318 (procymidone), C-224 (iprodione) or C-407 (vinclozolin). Preferred compound among these imide compounds is procymidone.

The present invention can control a variety of plant diseases, examples are described below. In the method of the invention, usually the composition of the invention is applied.

Blast (*Pyricularia oryzae*), Helminthosporium leaf spot (*Cochliobolus miyabeanus*) and sheath blight (*Rhizoctonia solani*) of rice plant; powdery mildew (*Erysiphe graminis*), scab (*Gibberella zeae*), rust (*Puccinia striiformis, P. graminis, P. recondita, P. hordei*), snow blight (Typhula sp., *Micronectriella nivalis*), loose smut (*Ustilago tritici, U. nuda*), bunt (*Tilletia caries*), eyespot (*Pseudocercosporella herpotrichoides*), scald (*Rhynchosporium secalis*), leaf blight (*Septoria tritici*) and glume blotch (*Leptosphaeria nodorum*) of barley, wheat, oats and rye; melanose (*Diaporthe citri*), scab (*Elsinoe fawcetti*) and pencillium rot (*Penicillium digitatum, P. italicum*) of citrus; blossom blight (*Sclerotinia mali*), canker (*Valsa mali*), powdery mildew (*Podosphaera leucotricha*), Alternaria leaf spot (*Al ternaria mali*) and scab (*Venturia inaequalis*) of apple; scab (*Venturia nashicola, V. pirina*), black spot (*Al ternaria kikuchiana*) and rust (*Gymnosporangium haraeanum*) of pear; brown rot (*Scierotinia cinerea*), scab (*Cladosporium carpophilum*) and Phomopsis rot (*Phomopsis sp.*) of peach; anthracnose (*Elsinoe ampelina*), ripe rot (*Glomerella cingulata*), powdery mildew (*Uncinula necator*), rust (*Phakopsora ampelopsidis*), black rot (*Guignardia bidwelii*) and downy mildew (*Plasmopara viticola*) of grape; anthracnose (*Gloeosporium kaki*) and leaf spot (*Cercospora kaki, Mycosphaerella nawae*) of Japanese persimmon; anthracnose (*Colletotrichum lagenarium*), powdery mildew (*Sphaerotheca fuliginea*), gummy stem blight (*Mycosphaerella melonis*), stem rot (*Fusarium oxysporum*), downy mildew (*Pseudoperonospora cubensis*), late bright (Phytophthora sp.) and damping-off (Pythium sp.) of melons and cucumbers; early blight (*Alternaria solani*), leaf mold (*Cladosporium fulvum*) and late blight (*Phytophthora infestans*) of tomato; brown spot(*Phomopsis vexans*) and powdery mildew (*Erysiphe cichoracearum*) of eggplant; altenaria leaf spot (*Alternaria japonica*) and white spot (*Cercosporella brassicae*) of vegetables of Cruciferae; Welsh onion rust (*Puccinia allii*); purple stain (*Cercospora kikuchii*), Sphaceloma scab (*Elsinoe glycines*) and pod and stem blight (*Diaporthe phaseolorum var. sojae*) of soybean; kidney bean anthracnose (*Colletotrichum lindemthianum*); early leaf spot (*Cercospora personata*) and leaf spot (*Cercospora arachidicola*) of peanut; pea powdery mildew (*Erysiphe pisi*); early blight (*Alternaria solani*) and late blight (*Phytophthora infestans*) of potate; strawberry powdery mildew (*Sphaerotheca humuli*); net blister blight (*Exobasidium reticulatum*) and white scab (*Elsinoe leucospila*) of tea plant; brown spot (*Alternaria longipes*), powdery mildew (*Erysiphe cichoracearum*), anthracnose (*Colletotrichum tabacum*), downy mildew (*Peronospora tabacina*) and (*Phytophthora nicotianae*) of tobacco; beet leaf spot (*Cercospora beticola*); black spot (*Diplocarpon rosae*) and powdery mildew (*Sphaerotheca pannosa*) of rose; leaf spot (*Septoria chrysanthemi-indici*) and white rust (*Puccinia horiana*) of chrysanthemum; gray mold (*Botrytis cinerea*) and stem rot (*Sclerotinia sclerotiorum*) of various crops and the like.

And also the composition of the invention can effectively control the fungi (plant diseases) which are tolerant to the imide compound such as procimidone, iprodione or vinclozolin.

In the composition of the invention, a weight ratio of at least one imide compound selected from the Compound (II), the Compound (III) and the Compound (IV), to the Compound (I), is usually 0.5 to 8:1, preferably 1 to 2:1.

In the case of applying the composition of the invention for the method of the invention, it is no problem applying merely a mixture (hereinafter, at least one imide compound and the Compound (I) together are referred to as the active ingredients of the invention) of at least one imide compound selected from the Compound (II), the Compound (III) and the Compound (IV), and the Compound (I), without other ingredient. But usually the composition of the invention may be applied in the form of formulations such as emulsifiable concentrates, flowables, granules, dry-flowables, wettable powders, aqueous liquid formulation, oil solution, smoking formulation, aerosol, micro capsule and the like which can be prepared by mixing the active ingredients of the invention with solid carriers, liquid carriers, gas carriers, surfactants and the like, and if necessary, adding other adjuvants such as adhesive agents, dispersing agent, stabilizers. In such a formulation, the active ingredients of the invention are usually included at the total amount of 0.1% to 99% by weight, preferably 0.2% to 90% by weight.

The solid carrier to be used in the formulation may include, for example, the following materials in fine powder or granule form: mineral materials (e.g., kaolinite clay, attapulgite clay, bentonite clay, montmorillonite clay, acid clay, pyrophyllite, talc, diatomaceous earth, calcite), natural organic materials (e.g., stalk of corn, powder of wallnutshell), synthetic organic materials (e.g., urea), salts (e.g., calcium carbonate, ammonium sulfate) and synthetic inorganic materials (e.g., synthetic hydrated silicon oxide). The liquid carrier may include, for example, aromatic hydrocarbons (e.g., xylene, alkylbenzene, methylnaphthalene), alcohols (e.g., isopropyl alcohol, ethylene glycol, propylene glycol, ethylene glycol mono-ethyl ether), ketones (e.g., acetone, cyclohexanone, isophorone), vegetable oils (e.g., soybean oil, cotton seeds oil), petroleum aliphatic hydrocarbons, esters, dimethyl sulufoxide, acetonitrile and water. The gas carrier may be include, for example, LPG (e.g., butane, propane), nitrogen, carbon dioxide. The surfactant may include, for example, anionic surfactants (e.g., alkylsulfate ester salts, alkyl(aryl)sulfonic acid salts, dialkylsulfosuccinic acid salts, phosphate salts of polyoxyethylenealkyl aryl ether, lignin sulfonic acid salts, naphthalenesulfonic acid formaldehyde condensations), nonionic surfactants (e.g., polyoxyethylene alkyl aryl ethers, polyoxyethylene propylene block copolymer, sorbitan fatty acid esters). The other adjuvants may include, for example, water-soluble polymers (e.g., polyvinyl alcohol, polyvinylpyrrolidone), polysaccharides (e.g., gum arabic, alginic acid and their salts, CMC (carboxy methyl cellulose), xanthan gum), inorganic materials (aluminum magnesium silicate, alumina sol), preservatives, coloring agents, PAP (isopropyl acid phosphate), BHT.

The composition of the invention can also be prepared by formulating each the active ingredient of the invention into an formulation with the style described above, and if necessary after diluting with water, and mixing the formulations separately formulated or the dilutions separately diluted.

The method of the invention, in which the composition of the invention is applied, is not limited to specified methods, when the composition of the invention can be substantially applied; for example, treatment of plant(s) such as foliar treatment, treatment of land where plant(s) is growing or will grow such as soil treatment, treatment of seeds of plant such as seeds disinfecting.

In the method of the invention, the application amount of the active ingredients of the invention; although it may vary with a variety of plants (crops) to be protected, a variety of plant diseases to be controlled, a extent of disease damage, a formulation type, an application type, application times, weather condition and the like; is usually 0.1 to 50 g per are, preferably 1 to 10 g per are. In the active ingredients of the invention, a weight ratio of at least one imide compound selected from the Compound (II), the Compound (III) and the Compound (IV), to the Compound (I), is usually 0.5 to 8:1, preferably 1 to 2:1.

In the case of emulsifiable concentrates, wettable powders, flowables and the like, they are usually applied after diluted with water, usually at a concentration of 0.0005% to 2%, preferably at a concentration of 0.005% to 1% as active ingredients of the invention. In the case of dust formulations, granules and the like, they are usually applied as it is without diluting. In the case of treatment of seeds, a amount of the active ingredients of the invention is usually 0.001 to 100 g per 1 kg of seeds, preferably 0.01 to 50 g per 1 kg of seeds.

The following is describe further the invention with formulation examples and test examples, but the present invention is not to be limited by the following examples.

FORMULATION EXAMPLE 1

Two point five (2.5) parts of the Compound (I-a), (I-b), (I-c), (I-d), (I-e), (I-f), (I-g), (I-h), (I-i), (I-j), (I-k), (I-l), (I-m), (I-n), (I-o) or (I-p), 2.5 parts of the Compound (II), 14 parts of polyoxyethylenestyryl phenyl ether, 6 parts of calcium dodecylbenzenesulfonate, and 75 parts of xylene are well mixed to give separately an emulsifiable concentrates.

FORMULATION EXAMPLE 2

Five (5) parts of the Compound (I-a), (I-b), (I-c), (I-d), (I-e), (I-f), (I-g), (I-h), (I-i), (I-j), (I-k), (I-l), (I-m), (I-n), (I-o) or (I-p), 5 parts of the Compound (II), 35 parts of a mixture of white carbons and ammonium polyoxyethylene-alkylethersulfate salts (the weight ratio is 1:1) and 55 parts of water are well mixed and wet pulverized to give separately a flowable.

FORMULATION EXAMPLE 3

Five (5) parts of the Compound (I-a), (I-b), (I-c), (I-d), (I-e), (I-f), (I-g), (I-h), (I-i), (I-j), (I-k), (I-l), (I-m), (I-n), (I-o) or (I-p), 10 parts of the Compound (II), 1.5 parts of sorbitan trioleate and 28.5 parts of an aqueous solution including 2 parts of polyvinyl alcohol are well mixed and wet pulverized. Then 45 parts of an aqueous solution including 0.05 part of xanthan gum and 0.1 part of aluminum magnesium silicate are added to the mixture, and 10 parts of propylene glycol are added, and the mixture is well mixed to give separately a flowable.

FORMULATION EXAMPLE 4

One (1) part of the Compound (I-a), (I-b), (I-c), (I-d), (I-e), (I-f), (I-g), (I-h), (I-i), (I-j), (I-k), (I-l), (I-m), (I-n), (I-o) or (I-p), 2.5 parts of the Compound (II), 1 part of synthetic hydrated silicon oxide, 2 parts of calcium lignin sulfonate, 30 parts of bentonite, and 63.5 parts of kaolinite clay are well pulverized, and water is added Then the mixture is well kneaded and granulated and dried to give separately a granule.

FORMULATION EXAMPLE 5

Twelve point five (12.5) parts of the Compound (I-a), (I-b), (I-c), (I-d), (I-e), (I-f), (I-g), (I-h), (I-i), (I-j), (I-k), (I-l), (I-m), (I-n), (I-o) or (I-p), 37.5 parts of the Compound (II), 3 parts of calcium lignin sulfonate, 2 parts of sodium laurylsulfate and 45 parts of synthetic hydrated silicon oxide are well pulverized and mixed to give separately a wettable powder.

FORMULATION EXAMPLE 6

One (1) part of the Compound (I-a), (I-b), (I-c), (I-d), (I-e), (I-f), (I-g), (I-h), (I-i), (I-j), (I-k), (I-l), (I-m), (I-n), (I-o) or (I-p), 2 parts of the Compound (II), 85 parts of kaolinite clay and 10 parts of talc are well pulverized and mixed to give separately a dust formulation.

Test Example 1

Plastic pots were filled with sandy loam and sown with cucumber (Sagamihanjiro), followed by growing in a greenhouse for 12 days. A wettable powder of the Compound (I-j) and a wettable powder of procymidone were separately diluted with water, and these dilutions were tank-mixed, then the tank-mixed dilution of the prescribed concentrations of the Compound (I-j) and procymidone was prepared. Said tank-mixed dilution was sprayed to foliage of said cucumber so as to adhere the dilution sufficiently to the surfaces of its leave. After air-drying, a PDA medium including hyphae of the fungi of gray mold of cucumber was placed on the leave surfaces of said cucumber. After inoculation, the plastic pots were placed under a humid environment of 10° C. for 6 days, and then the controlling effect was examined.

For comparison, the controlling effect, in the case of the treatment of the dilution of the prescribed concentration of the Compound (I-j) or procymidone, was examined in the same way.

And also for calculating the controlling value, the attack rate of non-treated plant was examined.

At the examination, the following evaluation indices was used. The attack rates were calculated with Scheme 1, and then on the basis of the attack rates, the controlling values were calculated with Scheme 2.

The results were described at Table 2.

Test Example 2–4

The similar tests were carried out with the Compound (I-i), the Compound (I-n) or the Compound (I-o), in place of the Compound (I-j).
Evaluation indices:
  0: a diameter of the morbid spot is 0 mm,
  1: 1 to 5 mm, 2: 5 to 10 mm, 3: 10 to 15 mm,
  4: 15 to 20 mm, 5: above 20 mm $$\text{Attack rate} = \frac{\sum (\text{evaluation index of examined leaf})}{(5 \times \text{number of examined leaves})} \times 100 \quad \text{Scheme 1}$$

Scheme 2

$$\text{Controlling value} = 100 \times (A-B)/A$$

A: Attack rate of non-treated plants
B: Attack rate of treated plants

The controlling effect, which is expected when treatment is carried out by mixing the given two species of active ingredient compounds, is generally calculated according to the following Colby equation described at Scheme 3.
Scheme 3

$$E = X + Y - (XY)/100I$$

X: Controlling value when the active ingredient compound A at M ppm was applied
Y: Controlling value when the active ingredient compound B at N ppm was applied
E: Expected controlling value when the active ingredient compound A at M ppm and compound B at N ppm were applied (hereinafter referred to as expected controlling value)

TABLE 2

| Test compound | Concentration of active ingredients (ppm) | Actual controlling value (%) | Expected controlling value (%) | Synergistic effect (%) |
|---|---|---|---|---|
| (I – i) + (II) | 2.5 + 5.0 | 80.0 | 35.0 | 228.6 |
| (I – i) | 2.5 | 35.0 | — | — |
| (I – j) + (II) | 2.5 + 5.0 | 85.0 | 50.0 | 170.0 |
| (I – j) | 2.5 | 50.0 | — | — |
| (I – n) + (II) | 2.5 + 5.0 | 82.5 | 47.5 | 173.7 |
| (I – n) | 2.5 | 47.5 | — | — |

TABLE 2-continued

| Test compound | Concentration of active ingredients (ppm) | Actual controlling value (%) | Expected controlling value (%) | Synergistic effect (%) |
| --- | --- | --- | --- | --- |
| (I − o) + (II) | 2.5 + 5.0 | 85.0 | 40.0 | 212.5 |
| (I − o) | 2.5 | 40.0 | — | — |
| (II) | 5.0 | 0 | — | — |

INDUSTRIAL APPLICABILITY

By the present invention, plant diseases can be controlled efficiently.

What is claimed is:

1. A plant diseases controlling composition containing:
   at least one imide compound selected from N-(3,5-dichlorophenyl)-1,2-dimethylcyclopropane-1,2-dicarboximide, 3-(3,5-dichlorophenyl)-N-(1-methylethyl)-2,4-dioxo-1-imidazolidinecarboxamide and 3-(3,5-dichlorophenyl)-5-methyl-5-vinyl-1,3-oxazolidine-2,4-dione; and
   the pyrazolinone compound represented by formula:

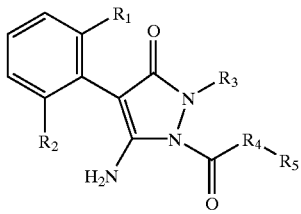

wherein
   $R_1$ represents halogen or methyl optionally substituted with halogen, $R_2$ represents hydrogen, halogen or methyl optionally substituted with halogen, $R_3$ represents isopropyl, sec-butyl, 1-ethylpropyl, 1-methylbutyl, tert-butyl or 1,1-dimethylpropyl, $R_4$ represents oxygen or sulfur and $R_5$ represents C1–C5 alkyl, C2–C5 alkynyl or C3–C5 alkenyl;
   as active ingredients.

2. The plant diseases controlling composition according to claim 1, wherein the weight ratio of the inside compound to the pyrazolinone compound is 0.5:1 to 8:1.

3. The plant diseases controlling composition according to claim 1, wherein the imide compound is N-(3,5-dichlorophenyl)-1,2-dimethylcyclopropane-1,2-dicarboximide.

4. The plant diseases controlling composition according to claim 1, wherein $R_1$ is halogen or methyl, $R_2$ is hydrogen or halogen, $R_3$ is isopropyl or sec-butyl, $R_4$ is oxygen or sulfur, and $R_5$ is C1–C5 alkyl or C3–C5 alkenyl.

5. The plant diseases controlling composition according to claim 1, wherein $R_1$ is chlorine or methyl, $R_2$ is hydrogen or chlorine, $R_3$ is isopropyl or sec-butyl, $R_4$ is oxygen or sulfur, and $R_5$ is ethyl or allyl.

6. A method of controlling plant diseases comprising applying:
   at least one imide compound selected from the group consisting of N-(3,5-dichlorophenyl)-1,2-dimethylcyclopropane-1,2-dicarboximide, 3-(3,5-dichlorophenyl)-N-(1-methylethyl)-2,4-dioxo-1-imidazolidinecarboxamide and 3-(3,5-dichlorophenyl)-5-methyl-5-vinyl-1,3-oxazolidine-2,4-dione; and
   the pyrazolinone compound represented by formula:

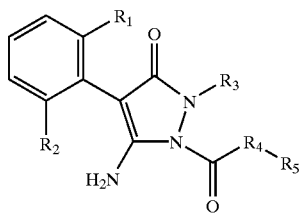

wherein
   $R_1$ represents halogen or methyl optionally substituted with halogen, $R_2$ represents hydrogen, halogen or methyl optionally substituted with halogen, $R_3$ represents isopropyl, sec-butyl, 1-ethylpropyl, 1-methylbutyl, tert-butyl or 1,1-dimethylpropyl, $R_4$ represents oxygen or sulfur and $R_5$ represents C1–C5 alkyl, C2–C5 alkynyl or C3–C5 alkenyl;
   to a plant, to land where a plant grows or to seeds of a plant.

7. The method according to claim 6, wherein the weight ratio of the imide compound to the pyrazolinone compound is 0.5:1 to 8:1.

8. The method according to claim 6 or 7, wherein the imide compound is N-(3,5-dichlorophenyl)-1,2-dimethylcyclopropane-1,2-dicarboximide.

9. The method of claim 6, wherein $R_1$ is halogen or methyl, $R_2$ is hydrogen or halogen, $R_3$ is isopropyl or sec-butyl, $R_4$ is oxygen or sulfur, and $R_5$ is C1–C5 alkyl or C3–C5 alkenyl.

10. The method of claim 6, wherein $R_1$ is chlorine or methyl, $R_2$ is hydrogen or chlorine, $R_3$ is isopropyl or sec-butyl, $R_4$ is oxygen or sulfur, and $R_5$ is ethyl or allyl.

* * * * *